US008641602B2

(12) United States Patent
Belson (10) Patent No.: US 8,641,602 B2
(45) Date of Patent: Feb. 4, 2014

(54) STEERABLE ENDOSCOPE AND IMPROVED METHOD OF INSERTION (75) Inventor: Amir Belson, Los Altos, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 13/535,979

(22) Filed: Jun. 28, 2012

(65) Prior Publication Data

US 2012/0271109 A1    Oct. 25, 2012

Related U.S. Application Data

(63) Continuation of application No. 11/129,093, filed on May 13, 2005, now Pat. No. 8,226,546, which is a continuation of application No. 10/229,189, filed on Aug. 26, 2002, now Pat. No. 7,044,907, which is a continuation of application No. 09/790,204, filed on Feb. 20, 2001, now Pat. No. 6,468,203.

(60) Provisional application No. 60/194,140, filed on Apr. 3, 2000.

(51) Int. Cl.
*A61B 1/00* (2006.01)
(52) U.S. Cl.
USPC ............ 600/114; 600/141; 600/146; 600/152
(58) Field of Classification Search
USPC .................................. 600/117, 407, 424, 427
See application file for complete search history.

(56) References Cited

U.S. PATENT DOCUMENTS

| 616,672 | A | 12/1898 | Kelling |
| 2,510,198 | A | 6/1950 | Tesmer |
| 2,533,494 | A | 12/1950 | Mitchell, Jr. |
| 2,767,705 | A | 10/1956 | Moore |
| 3,060,972 | A | 10/1962 | Sheldon |
| 3,071,161 | A | 1/1963 | Ulrich |

(Continued)

FOREIGN PATENT DOCUMENTS

| DE | 2823025 C2 | 2/1986 |
| DE | 3707787 A1 | 9/1988 |

(Continued)

OTHER PUBLICATIONS

Belson et al., U.S. Appl. No. 11/796,220 entitled "Steerable segmented endoscope and method of insertion" filed Apr. 27, 2007.

(Continued)

*Primary Examiner* — Matthew J Kasztejna (57) ABSTRACT

A steerable endoscope has an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body that allows it to negotiate tortuous curves along a desired path through, around, and between organs within the body.

16 Claims, 7 Drawing Sheets

(56) References Cited

U.S. PATENT DOCUMENTS

| | | | |
|---|---|---|---|
| 3,096,962 A | 7/1963 | Meijs | |
| 3,162,214 A | 12/1964 | Bazinet | |
| 3,168,274 A | 2/1965 | Street | |
| 3,190,286 A | 6/1965 | Stokes | |
| 3,266,059 A | 8/1966 | Stelle | |
| 3,430,662 A | 3/1969 | Guarnaschelli | |
| 3,497,083 A | 2/1970 | Anderson | |
| 3,546,961 A | 12/1970 | Marton | |
| 3,610,231 A | 10/1971 | Takahashi et al. | |
| 3,625,084 A | 12/1971 | Siebert | |
| 3,643,653 A | 2/1972 | Takahashi et al. | |
| 3,739,770 A | 6/1973 | Mori | |
| 3,773,034 A | 11/1973 | Burns et al. | |
| 3,780,740 A | 12/1973 | Rhea | |
| 3,858,578 A | 1/1975 | Milo | |
| 3,871,358 A | 3/1975 | Fukuda et al. | |
| 3,897,775 A | 8/1975 | Furihata | |
| 3,913,565 A | 10/1975 | Kawahara | |
| 3,946,727 A | 3/1976 | Okada et al. | |
| 3,990,434 A | 11/1976 | Free | |
| 4,054,128 A | 10/1977 | Seufert et al. | |
| 4,176,662 A | 12/1979 | Frazer | |
| 4,233,981 A | 11/1980 | Schomacher | |
| 4,236,509 A | 12/1980 | Takahashi et al. | |
| 4,240,435 A | 12/1980 | Yazawa et al. | |
| 4,273,111 A | 6/1981 | Tsukaya | |
| 4,327,711 A | 5/1982 | Takagi | |
| 4,366,810 A | 1/1983 | Slanetz, Jr. | |
| 4,393,728 A | 7/1983 | Larson et al. | |
| 4,432,349 A | 2/1984 | Oshiro | |
| 4,483,326 A | 11/1984 | Yamaka et al. | |
| 4,489,826 A | 12/1984 | Dubson | |
| 4,494,417 A | 1/1985 | Larson et al. | |
| 4,499,895 A | 2/1985 | Takayama | |
| 4,503,842 A | 3/1985 | Takayama | |
| 4,517,652 A | 5/1985 | Bennett et al. | |
| 4,543,090 A | 9/1985 | McCoy | |
| 4,551,061 A | 11/1985 | Olenick | |
| 4,559,928 A | 12/1985 | Takayama | |
| 4,566,843 A | 1/1986 | Iwatsuka et al. | |
| 4,577,621 A | 3/1986 | Patel | |
| 4,592,341 A | 6/1986 | Omagari et al. | |
| 4,601,283 A | 7/1986 | Chikama | |
| 4,621,618 A | 11/1986 | Omagari | |
| 4,624,243 A | 11/1986 | Lowery et al. | |
| 4,630,649 A | 12/1986 | Oku | |
| 4,643,184 A | 2/1987 | Mobin-Uddin | |
| 4,646,722 A | 3/1987 | Silverstein et al. | |
| 4,648,733 A | 3/1987 | Merkt | |
| 4,651,718 A | 3/1987 | Collins et al. | |
| 4,655,257 A | 4/1987 | Iwashita | |
| 4,683,773 A | 8/1987 | Diamond | |
| 4,686,963 A | 8/1987 | Cohen et al. | |
| 4,712,969 A | 12/1987 | Kimura | |
| 4,726,355 A | 2/1988 | Okada | |
| 4,753,222 A | 6/1988 | Morishita | |
| 4,753,223 A | 6/1988 | Bremer | |
| 4,754,909 A | 7/1988 | Barker et al. | |
| 4,784,117 A | 11/1988 | Miyazaki | |
| 4,787,369 A | 11/1988 | Allred, III | |
| 4,788,967 A | 12/1988 | Ueda | |
| 4,793,326 A | 12/1988 | Shishido | |
| 4,796,607 A | 1/1989 | Allred, III | |
| 4,799,474 A | 1/1989 | Ueda | |
| 4,800,890 A | 1/1989 | Cramer | |
| 4,807,593 A | 2/1989 | Ito | |
| 4,815,450 A | 3/1989 | Patel | |
| 4,832,473 A | 5/1989 | Ueda | |
| 4,834,068 A | 5/1989 | Gottesman | |
| 4,873,965 A | 10/1989 | Danieli | |
| 4,873,990 A | 10/1989 | Holmes et al. | |
| 4,879,991 A | 11/1989 | Ogiu | |
| 4,884,557 A | 12/1989 | Takehana et al. | |
| 4,890,602 A | 1/1990 | Hake | |
| 4,895,431 A | 1/1990 | Tsujiuchi et al. | |
| 4,899,731 A | 2/1990 | Takayama et al. | |
| 4,904,048 A | 2/1990 | Sogawa et al. | |
| 4,917,114 A | 4/1990 | Green et al. | |
| 4,919,112 A | 4/1990 | Siegmund | |
| 4,930,494 A | 6/1990 | Takehana et al. | |
| 4,949,927 A | 8/1990 | Madocks et al. | |
| 4,957,486 A | 9/1990 | Davis | |
| 4,969,709 A | 11/1990 | Sogawa et al. | |
| 4,971,035 A | 11/1990 | Ito | |
| 4,977,886 A | 12/1990 | Takehana et al. | |
| 4,977,887 A | 12/1990 | Gouda | |
| 4,987,314 A | 1/1991 | Gotanda et al. | |
| 5,005,558 A | 4/1991 | Aomori | |
| 5,005,559 A | 4/1991 | Blanco et al. | |
| 5,014,709 A | 5/1991 | Bjelkhagen et al. | |
| 5,018,509 A | 5/1991 | Suzuki et al. | |
| 5,025,778 A | 6/1991 | Silverstein et al. | |
| 5,060,632 A | 10/1991 | Hibino et al. | |
| 5,092,901 A | 3/1992 | Hunter et al. | |
| 5,125,395 A | 6/1992 | Adair | |
| 5,127,393 A | 7/1992 | McFarlin et al. | |
| 5,159,446 A | 10/1992 | Hibino et al. | |
| 5,174,276 A | 12/1992 | Crockard | |
| 5,174,277 A | 12/1992 | Matsumaru | |
| 5,188,111 A | 2/1993 | Yates et al. | |
| 5,203,319 A | 4/1993 | Danna et al. | |
| 5,207,695 A | 5/1993 | Trout, III | |
| 5,217,001 A | 6/1993 | Nakao et al. | |
| 5,220,911 A | 6/1993 | Tamura | |
| 5,228,429 A | 7/1993 | Hatano | |
| 5,234,448 A | 8/1993 | Wholey et al. | |
| 5,243,967 A | 9/1993 | Hibino | |
| 5,250,058 A | 10/1993 | Miller et al. | |
| 5,251,611 A | 10/1993 | Zehel et al. | |
| 5,253,647 A | 10/1993 | Takahashi et al. | |
| 5,254,809 A | 10/1993 | Martin | |
| 5,257,617 A | 11/1993 | Takahashi | |
| 5,259,364 A | 11/1993 | Bob et al. | |
| 5,271,381 A | 12/1993 | Ailinger et al. | |
| 5,271,382 A | 12/1993 | Chikama | |
| 5,279,610 A | 1/1994 | Park et al. | |
| 5,297,443 A | 3/1994 | Wentz | |
| 5,325,845 A | 7/1994 | Adair | |
| 5,337,732 A | 8/1994 | Grundfest et al. | |
| 5,337,733 A | 8/1994 | Bauerfeind et al. | |
| 5,343,874 A | 9/1994 | Picha et al. | |
| 5,347,987 A | 9/1994 | Feldstein et al. | |
| 5,348,259 A | 9/1994 | Blanco et al. | |
| 5,370,108 A | 12/1994 | Miura et al. | |
| 5,383,467 A | 1/1995 | Auer et al. | |
| 5,383,852 A | 1/1995 | Stevens-Wright | |
| 5,389,222 A | 2/1995 | Shahinpoor | |
| 5,394,864 A | 3/1995 | Kobayashi et al. | |
| 5,400,769 A | 3/1995 | Tanii et al. | |
| 5,402,768 A | 4/1995 | Adair | |
| 5,411,508 A | 5/1995 | Bessler et al. | |
| 5,413,108 A | 5/1995 | Alfano | |
| 5,421,337 A | 6/1995 | Richards-Kortum et al. | |
| 5,425,738 A | 6/1995 | Gustafson et al. | |
| 5,429,118 A | 7/1995 | Cole et al. | |
| 5,439,000 A | 8/1995 | Gunderson et al. | |
| 5,456,714 A | 10/1995 | Owen | |
| 5,460,166 A | 10/1995 | Yabe et al. | |
| 5,460,168 A | 10/1995 | Masubuchi et al. | |
| 5,469,840 A | 11/1995 | Tanii et al. | |
| 5,482,029 A | 1/1996 | Sekiguchi et al. | |
| 5,487,757 A | 1/1996 | Truckai et al. | |
| 5,507,287 A | 4/1996 | Palcic et al. | |
| 5,507,717 A | 4/1996 | Kura et al. | |
| 5,522,788 A | 6/1996 | Kuzmak | |
| 5,531,664 A | 7/1996 | Adachi et al. | |
| 5,551,945 A | 9/1996 | Yabe et al. | |
| 5,558,619 A | 9/1996 | Kami et al. | |
| 5,558,665 A | 9/1996 | Kieturakis | |
| 5,577,992 A | 11/1996 | Chiba et al. | |
| 5,586,968 A | 12/1996 | Grundl et al. | |
| 5,590,660 A | 1/1997 | MacAulay et al. | |
| 5,601,087 A | 2/1997 | Gunderson et al. | |
| 5,602,449 A | 2/1997 | Krause et al. | |

(56) References Cited

U.S. PATENT DOCUMENTS

| | | | |
|---|---|---|---|
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,647,368 A | 7/1997 | Zeng et al. |
| 5,647,840 A | 7/1997 | Damelio et al. |
| 5,651,769 A | 7/1997 | Waxman et al. |
| 5,658,238 A | 8/1997 | Suzuki et al. |
| 5,662,587 A | 9/1997 | Grundfest et al. |
| 5,665,050 A | 9/1997 | Benecke |
| 5,667,476 A | 9/1997 | Frassica et al. |
| 5,679,216 A | 10/1997 | Takayama et al. |
| 5,681,260 A * | 10/1997 | Ueda et al. ................. 600/114 |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,762,613 A | 6/1998 | Sutton et al. |
| 5,765,561 A | 6/1998 | Chen et al. |
| 5,769,792 A | 6/1998 | Palcic et al. |
| 5,772,597 A | 6/1998 | Goldberger et al. |
| 5,773,835 A | 6/1998 | Sinofsky |
| 5,779,624 A | 7/1998 | Chang |
| 5,807,241 A | 9/1998 | Heimberger |
| 5,810,715 A | 9/1998 | Moriyama |
| 5,810,716 A | 9/1998 | Mukherjee et al. |
| 5,810,717 A | 9/1998 | Maeda et al. |
| 5,813,976 A | 9/1998 | Filipi et al. |
| 5,827,190 A | 10/1998 | Palcic et al. |
| 5,842,973 A | 12/1998 | Bullard |
| 5,860,581 A | 1/1999 | Robertson et al. |
| 5,860,914 A | 1/1999 | Chiba et al. |
| 5,876,329 A | 3/1999 | Harhen |
| 5,876,373 A | 3/1999 | Giba et al. |
| 5,885,208 A | 3/1999 | Moriyama |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,916,147 A | 6/1999 | Boury |
| 5,921,915 A | 7/1999 | Aznoian et al. |
| 5,928,136 A | 7/1999 | Barry |
| 5,941,815 A | 8/1999 | Chang |
| 5,941,908 A | 8/1999 | Goldsteen et al. |
| 5,957,833 A | 9/1999 | Shan |
| 5,968,052 A | 10/1999 | Sullivan, III |
| 5,971,767 A | 10/1999 | Kaufman et al. |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,996,346 A | 12/1999 | Maynard |
| 6,016,440 A | 1/2000 | Simon et al. |
| 6,033,359 A | 3/2000 | Doi |
| 6,036,636 A | 3/2000 | Motoki et al. |
| 6,042,155 A | 3/2000 | Lockwood |
| 6,048,307 A | 4/2000 | Grundl et al. |
| 6,066,102 A | 5/2000 | Townsend et al. |
| 6,066,132 A | 5/2000 | Chen et al. |
| 6,096,289 A | 8/2000 | Goldenberg |
| 6,099,464 A | 8/2000 | Shimizu et al. |
| 6,099,485 A | 8/2000 | Patterson |
| 6,106,510 A | 8/2000 | Lunn et al. |
| 6,119,913 A | 9/2000 | Adams et al. |
| 6,129,667 A | 10/2000 | Dumoulin et al. |
| 6,129,683 A | 10/2000 | Sutton et al. |
| 6,141,577 A | 10/2000 | Rolland et al. |
| 6,149,581 A | 11/2000 | Klingenstein |
| 6,162,171 A | 12/2000 | Ng et al. |
| 6,174,280 B1 | 1/2001 | Oneda et al. |
| 6,174,291 B1 | 1/2001 | McMahon et al. |
| 6,179,776 B1 | 1/2001 | Adams et al. |
| 6,201,989 B1 | 3/2001 | Whitehead et al. |
| 6,203,493 B1 | 3/2001 | Ben-Haim |
| 6,203,494 B1 | 3/2001 | Moriyama |
| 6,210,337 B1 | 4/2001 | Dunham et al. |
| 6,221,006 B1 | 4/2001 | Dubrul et al. |
| 6,233,476 B1 * | 5/2001 | Strommer et al. ............ 600/424 |
| 6,241,657 B1 | 6/2001 | Chen et al. |
| 6,249,076 B1 | 6/2001 | Madden et al. |
| 6,270,453 B1 | 8/2001 | Sakai |
| 6,306,081 B1 | 10/2001 | Ishikawa et al. |
| 6,309,346 B1 | 10/2001 | Farhadi |
| 6,315,714 B1 | 11/2001 | Akiba |
| 6,319,197 B1 | 11/2001 | Tsuji et al. |
| 6,327,492 B1 | 12/2001 | Lemelson |
| 6,332,089 B1 | 12/2001 | Acker et al. |
| 6,348,058 B1 | 2/2002 | Melkent et al. |
| 6,352,503 B1 | 3/2002 | Matsui et al. |
| 6,366,799 B1 | 4/2002 | Acker et al. |
| 6,402,687 B1 | 6/2002 | Ouchi |
| 6,408,889 B1 | 6/2002 | Komachi |
| 6,453,190 B1 | 9/2002 | Acker et al. |
| 6,459,481 B1 | 10/2002 | Schaack |
| 6,468,203 B2 | 10/2002 | Belson |
| 6,482,149 B1 | 11/2002 | Torii |
| 6,485,413 B1 | 11/2002 | Boppart et al. |
| 6,490,467 B1 | 12/2002 | Bucholz et al. |
| 6,511,417 B1 | 1/2003 | Taniguchi et al. |
| 6,511,418 B2 | 1/2003 | Shahidi et al. |
| 6,517,477 B1 | 2/2003 | Wendlandt |
| 6,527,706 B2 | 3/2003 | Ide |
| 6,537,211 B1 | 3/2003 | Wang et al. |
| 6,544,215 B1 | 4/2003 | Bencini et al. |
| 6,554,793 B1 | 4/2003 | Pauker et al. |
| 6,569,173 B1 | 5/2003 | Blatter et al. |
| 6,610,007 B2 | 8/2003 | Belson et al. |
| 6,616,600 B2 | 9/2003 | Pauker |
| 6,638,213 B2 | 10/2003 | Ogura et al. |
| 6,641,528 B2 | 11/2003 | Torii |
| 6,656,110 B1 | 12/2003 | Irion et al. |
| 6,699,183 B1 | 3/2004 | Wimmer |
| 6,761,685 B2 | 7/2004 | Adams et al. |
| 6,783,491 B2 | 8/2004 | Saadat et al. |
| 6,790,173 B2 | 9/2004 | Saadat et al. |
| 6,800,056 B2 | 10/2004 | Tartaglia et al. |
| 6,817,973 B2 | 11/2004 | Merril et al. |
| 6,843,793 B2 | 1/2005 | Brock et al. |
| 6,858,005 B2 | 2/2005 | Ohline et al. |
| 6,869,396 B2 | 3/2005 | Belson |
| 6,902,528 B1 | 6/2005 | Garibaldi et al. |
| 6,960,161 B2 | 11/2005 | Amling et al. |
| 6,974,411 B2 | 12/2005 | Belson |
| 6,984,203 B2 | 1/2006 | Tartaglia et al. |
| 7,018,331 B2 | 3/2006 | Chang et al. |
| 7,087,013 B2 | 8/2006 | Belson et al. |
| 7,167,180 B1 | 1/2007 | Shibolet |
| 2001/0000040 A1 | 3/2001 | Adams et al. |
| 2002/0022765 A1 | 2/2002 | Belson |
| 2002/0062062 A1 | 5/2002 | Belson et al. |
| 2002/0120178 A1 | 8/2002 | Tartaglia et al. |
| 2002/0120254 A1 | 8/2002 | Julian et al. |
| 2002/0147385 A1 | 10/2002 | Butler et al. |
| 2002/0161281 A1 | 10/2002 | Jaffe et al. |
| 2002/0193661 A1 | 12/2002 | Belson |
| 2002/0193662 A1 | 12/2002 | Belson |
| 2003/0045778 A1 | 3/2003 | Ohline et al. |
| 2003/0083550 A1 | 5/2003 | Miyagi |
| 2003/0130598 A1 | 7/2003 | Manning et al. |
| 2003/0149338 A1 | 8/2003 | Francois et al. |
| 2003/0167007 A1 | 9/2003 | Belson |
| 2003/0195387 A1 | 10/2003 | Kortenbach et al. |
| 2003/0233027 A1 | 12/2003 | Ewers et al. |
| 2003/0233056 A1 | 12/2003 | Saadat et al. |
| 2003/0233057 A1 | 12/2003 | Saadat et al. |
| 2003/0233058 A1 | 12/2003 | Ewers et al. |
| 2003/0233066 A1 | 12/2003 | Ewers et al. |
| 2003/0236505 A1 | 12/2003 | Bonadio et al. |
| 2003/0236549 A1 | 12/2003 | Bonadio et al. |
| 2004/0019254 A1 | 1/2004 | Belson et al. |
| 2004/0044270 A1 | 3/2004 | Barry |

(56) References Cited

U.S. PATENT DOCUMENTS

| | | |
|---|---|---|
| 2004/0106852 A1 | 6/2004 | Windheuser et al. |
| 2004/0176683 A1 | 9/2004 | Whitin et al. |
| 2004/0193008 A1 | 9/2004 | Jaffe et al. |
| 2004/0193009 A1 | 9/2004 | Jaffe et al. |
| 2004/0210109 A1 | 10/2004 | Jaffe et al. |
| 2004/0220450 A1 | 11/2004 | Jaffe et al. |
| 2005/0020901 A1 | 1/2005 | Belson et al. |
| 2005/0085693 A1 | 4/2005 | Belson et al. |
| 2005/0124855 A1 | 6/2005 | Jaffe et al. |
| 2005/0154258 A1 | 7/2005 | Tartaglia et al. |
| 2005/0154261 A1 | 7/2005 | Ohline et al. |
| 2005/0165276 A1 | 7/2005 | Belson et al. |
| 2005/0209509 A1 | 9/2005 | Belson |
| 2005/0222497 A1 | 10/2005 | Belson |
| 2006/0009678 A1 | 1/2006 | Jaffe et al. |
| 2006/0052664 A1 | 3/2006 | Julian et al. |
| 2006/0235457 A1 | 10/2006 | Belson |
| 2006/0235458 A1 | 10/2006 | Belson |
| 2006/0258912 A1 | 11/2006 | Belson et al. |
| 2007/0043259 A1 | 2/2007 | Jaffe et al. |
| 2007/0093858 A1 | 4/2007 | Gambale et al. |
| 2007/0135803 A1 | 6/2007 | Belson |
| 2007/0161291 A1 | 7/2007 | Swinehart et al. |
| 2007/0161857 A1 | 7/2007 | Durant et al. |
| 2007/0249901 A1 | 10/2007 | Ohline et al. |
| 2007/0270650 A1 | 11/2007 | Eno et al. |
| 2008/0045794 A1 | 2/2008 | Belson |
| 2009/0099420 A1 | 4/2009 | Woodley et al. |
| 2010/0094088 A1 | 4/2010 | Ohline et al. |

FOREIGN PATENT DOCUMENTS

| | | |
|---|---|---|
| DE | 4102211 A1 | 8/1991 |
| DE | 19626433 A1 | 1/1998 |
| DE | 19729499 A1 | 1/1999 |
| EP | 165718 A2 | 12/1985 |
| EP | 382974 A1 | 8/1990 |
| EP | 497781 B1 | 1/1994 |
| EP | 1101442 A2 | 5/2001 |
| FR | 2732225 A1 | 10/1996 |
| GB | 2347685 A | 9/2000 |
| IE | 20000225 | 3/2000 |
| JP | 4712705 | 5/1972 |
| JP | 63136014 A2 | 6/1988 |
| JP | 63272322 A2 | 11/1988 |
| JP | 1152413 A2 | 6/1989 |
| JP | 1229220 A2 | 9/1989 |
| JP | 1262372 A2 | 10/1989 |
| JP | 2246986 A2 | 10/1990 |
| JP | 2296209 A2 | 12/1990 |
| JP | 3136630 A2 | 6/1991 |
| JP | 4054970 A2 | 2/1992 |
| JP | 5001999 A2 | 1/1993 |
| JP | 5011196 A2 | 1/1993 |
| JP | 5111458 A2 | 5/1993 |
| JP | 5305073 A2 | 11/1993 |
| JP | 6007287 A2 | 1/1994 |
| JP | 7116104 A2 | 5/1995 |
| JP | 8322786 A2 | 12/1996 |
| JP | 9028662 A2 | 2/1997 |
| JP | 10337274 A2 | 12/1998 |
| JP | 11042258 A2 | 2/1999 |
| JP | 21046318 A2 | 2/2001 |
| JP | 3322356 | 9/2002 |
| SU | 871786 A1 | 10/1981 |
| SU | 1256955 A1 | 9/1986 |
| SU | 1301701 A1 | 4/1987 |
| WO | 9317751 A1 | 9/1993 |
| WO | 9419051 A1 | 9/1994 |
| WO | 9504556 A2 | 2/1995 |
| WO | 9710746 A1 | 3/1997 |
| WO | 9824017 A2 | 6/1998 |
| WO | 9933392 A1 | 7/1999 |
| WO | 9951283 A2 | 10/1999 |
| WO | 9959664 A1 | 11/1999 |
| WO | 0027462 A1 | 5/2000 |
| WO | 0054653 A1 | 9/2000 |
| WO | 0074565 A1 | 12/2000 |
| WO | 0149353 A2 | 7/2001 |
| WO | 0167964 A2 | 9/2001 |
| WO | 0170096 A1 | 9/2001 |
| WO | 0170097 A1 | 9/2001 |
| WO | 0174235 A1 | 10/2001 |
| WO | 0180935 A1 | 11/2001 |
| WO | 0224058 A2 | 3/2002 |
| WO | 0239909 A1 | 5/2002 |
| WO | 02064028 A1 | 8/2002 |
| WO | 02068988 A1 | 9/2002 |
| WO | 02069841 A2 | 9/2002 |
| WO | 02096276 A1 | 12/2002 |
| WO | 03028547 A2 | 4/2003 |
| WO | 03073920 A2 | 9/2003 |
| WO | 03092476 A2 | 11/2003 |
| WO | 2004006980 A2 | 1/2004 |
| WO | 2004049905 A2 | 6/2004 |
| WO | 2004071284 A1 | 8/2004 |
| WO | 2004080313 A1 | 9/2004 |
| WO | 2004084702 A2 | 10/2004 |

OTHER PUBLICATIONS

Berger, W. L. et al., "Sigmoid Stiffener for Decompression Tube Placement in Colonic Pseudo-Obstruction," Endoscopy, 2000, vol. 32, Issue 1, pp. 54-57.

Hasson, H.M., "Technique of Open Laparoscopy," (from step 1 to step 9), May 1979, 2424 North Clark Street, Chicago, Illinois 60614, 3 pages.

International Search Report for Application No. PCT/US2001/10907, mailed on Aug. 28, 2001, 3 pages.

Laptop Magazine, Science & Technology section, Oct. 2002, pp. 98, 100, and 102.

Lee, Thomas S. et al., "A highly redundant robot system for inspection," Proceedings of Conference on Intelligent Robotics in Field, Factory, Service, and Space (CIRFFSS '94). Mar. 21-24, 1994. vol. 1, pp. 142-148. Houston, Texas.

McKernan, J.B. et al., "Laparoscopic general surgery," Journal of the Medical Association of Georgia, Mar. 1990, vol. 79, Issue 3, pp. 157-159.

Ohline et al., U.S. Appl. No. 12/425,272 entitled "Tendon-driven endoscope and methods of use," filed Apr. 16, 2009.

Slatkin, A.B. et al., "The development of a robotic endoscope," Proceedings 1995 IEEE/RSJ International Conference on Intelligent Robots and Systems, Aug. 5-9, 1995, vol. 2, pp. 162-171, Pittsburgh, Pennsylvania.

Woodley et al., U.S. Appl. No. 11/871,104 entitled "System for managing bowden cables in articulating instruments," filed Oct. 11, 2007.

\* cited by examiner

STEERABLE ENDOSCOPE AND IMPROVED METHOD OF INSERTION

CROSS-REFERENCE TO OTHER APPLICATIONS

The present application is a continuation of U.S. application Ser. No. 11/129,093, filed May 13, 2005, now U.S. Pat. No. 8,226,546, which is a continuation of U.S. application Ser. No. 10/229,189, filed Aug. 26, 2002, now U.S. Pat. No. 7,044,907, which is a continuation of U.S. application Ser. No. 09/790,204, filed Feb. 20, 2001, now U.S. Pat. No. 6,468,203, which claims priority of U.S. Provisional Application No. 60/194,140, filed Apr. 3, 2000, the entire contents of each of which is incorporated by reference herein.

FIELD OF THE INVENTION

The present invention relates generally to endoscopes and endoscopic medical procedures. More particularly, it relates to a method and apparatus to facilitate insertion of a flexible endoscope along a tortuous path, such as for colonoscopic examination and treatment.

BACKGROUND OF THE INVENTION

An endoscope is a medical instrument for visualizing the interior of a patient's body. Endoscopes can be used for a variety of different diagnostic and interventional procedures, including colonoscopy, bronchoscopy, thoracoscopy, laparoscopy and video endoscopy.

Colonoscopy is a medical procedure in which a flexible endoscope, or colonoscope, is inserted into a patient's colon for diagnostic examination and/or surgical treatment of the colon. A standard colonoscope is typically 135-185 cm in length and 12-13 mm in diameter, and includes a fiberoptic imaging bundle, illumination fibers and one or two instrument channels that may also be used for insufflation or irrigation. The colonoscope is inserted via the patient's anus and is advanced through the colon, allowing direct visual examination of the colon, the ileocecal valve and portions of the terminal ileum. Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complications, such as intestinal perforation. Steerable colonoscopes have been devised to facilitate selection of the correct path though the curves of the colon. However, as the colonoscope is inserted farther and farther into the colon, it becomes more difficult to advance the colonoscope along the selected path. At each turn, the wall of the colon Must maintain the curve in the colonoscope. The colonoscope rubs against the mucosal surface of the colon along the outside of each turn. Friction and slack in the colonoscope build up at each turn, making it more and more difficult to advance and withdraw the colonoscope. In addition, the force against the wall of the colon increases with the buildup of friction. In cases of extreme tortuosity, it may become impossible to advance the colonoscope all of the way through the colon.

Steerable endoscopes, catheters and insertion devices for medical examination or treatment of internal body structures are described in the following U.S. patents, the disclosures of which are hereby incorporated by reference in their entirety: U.S. Pat. Nos. 4,753,223; 5,337,732; 5,662,587; 4,543,090; 5,383,852; 5,487,757 and 5,337,733.

SUMMARY OF THE INVENTION

In keeping with the foregoing discussion, the present invention takes the form of a steerable endoscope for negotiating tortuous paths through a patient's body. The steerable endoscope can be used for a variety of different diagnostic and interventional procedures, including colonoscopy, bronchoscopy, thoracoscopy, laparoscopy and video endoscopy. The steerable endoscope is particularly well suited for negotiating the tortuous curves encountered when performing a colonoscopy procedure.

The steerable endoscope has anelongated body with a manually or selectively steerable distal portion and an automatically controlled proximal portion. The selectively steerable distal portion can be selectively steered or bent up to a full 180 degree bend in any direction. A fiberoptic imaging bundle and one or more illumination fibers extend through the body from the proximal end to the distal end. Alternatively, the endoscope can be configured as a video endoscope with a miniaturized video camera, such as a CCD camera, which transmits images to a video monitor by a transmission cable or by wireless transmission. Optionally, the endoscope may include one or two instrument channels that may also be used for insufflation or irrigation.

A proximal handle attached to the elongate body includes an ocular for direct viewing and/or for connection to a video camera, a connection to an illumination source and one or more luer lock fittings that are connected to the instrument channels. The handle is connected to a steering control for selectively steering or bending the selectively steerable distal portion in the desired direction and to an electronic motion controller for controlling the automatically controlled proximal portion of the endoscope. An axial motion transducer is provided to measure the axial motion of the endoscope body as it is advanced and withdrawn. Optionally, the endoscope may include a motor or linear actuator for automatically advancing and withdrawing the endoscope.

The method of the present invention involves inserting the distal end of the endoscope body into a patient, either through a natural orifice or through an incision, and steering the selectively steerable distal portion to select a desired path. When the endoscope body is advanced, the electronic motion controller operates the automatically controlled proximal portion of the body to assume the selected curve of the selectively steerable distal portion. This process is repeated by selecting another desired path with the selectively steerable distal portion and advancing the endoscope body again. As the endoscope body is further advanced, the selected curves propagate proximally along the endoscope body. Similarly, when the endoscope body is withdrawn proximally, the selected curves propagate distally along the endoscope body. This creates a sort of serpentine motion in the endoscope body that allows it to negotiate tortuous curves along a desired path through or around and between organs within the body.

The method can be used for performing colonoscopy or other endoscopic procedures, such as bronchoscopy, thoracoscopy, laparoscopy and video endoscopy. In addition, the apparatus and methods of the present invention can be used for inserting other types of instruments, such as surgical instruments, catheters or introducers, along a desired path within the body.

DETAILED DESCRIPTION OF THE INVENTION

Figure 1:
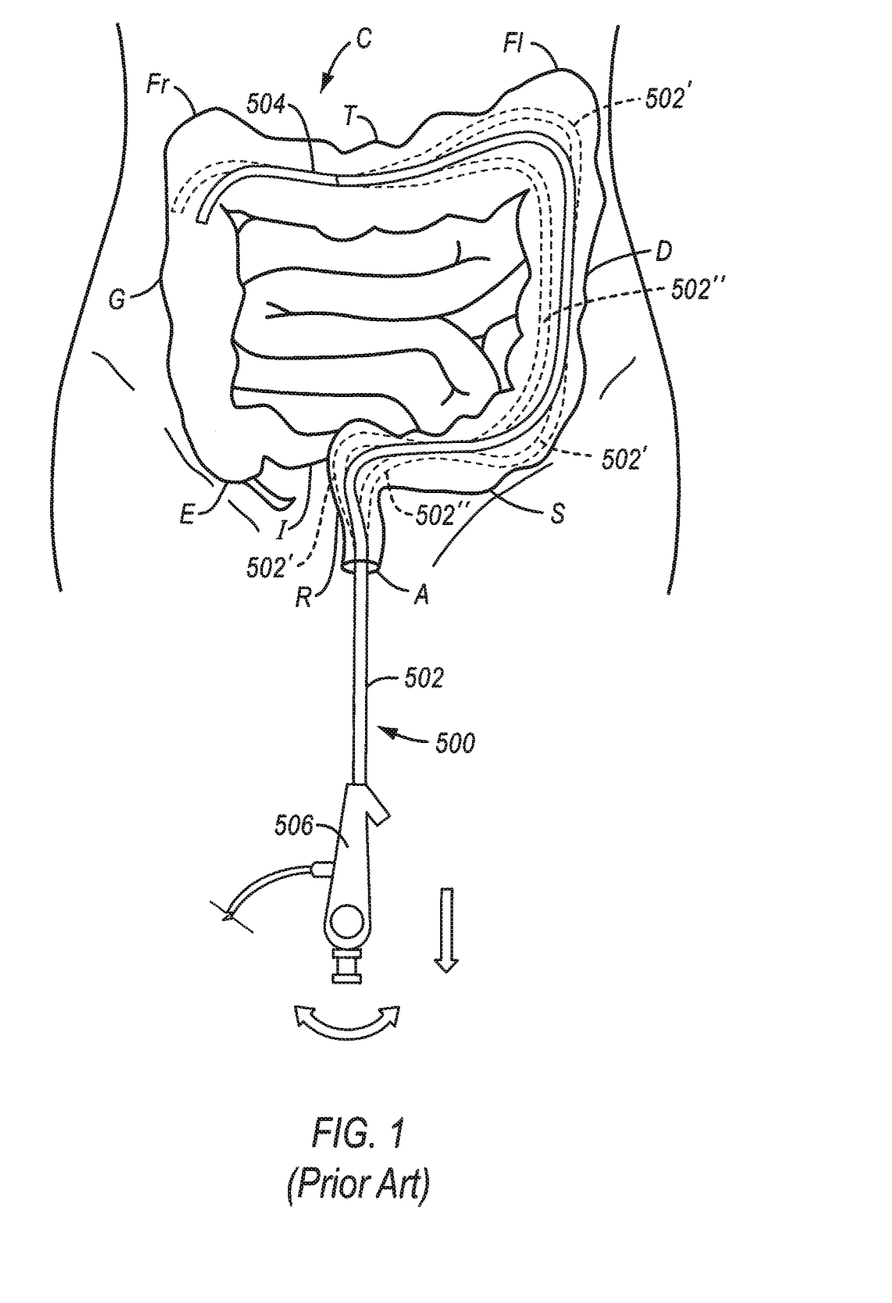
FIG. 1 shows a prior art colonoscope being employed for a colonoscopic examination of a patient's colon.

FIG. 1 shows a prior art colonoscope 500 being employed for a colonoscopic examination of a patient's colon C. The colonoscope 500 has a proximal handle 506 and an elongate body 502 with a steerable distal portion 504. The body 502 of the colonoscope 500 has been lubricated and inserted into the colon C via the patient's anus A. Utilizing the steerable distal portion 504 for guidance, the body 502 of the colonoscope 500 has been maneuvered through several turns in the patient's colon C to the ascending colon G. Typically, this involves a considerable amount of manipulation by pushing, pulling and rotating the colonoscope 500 from the proximal end to advance it through the turns of the colon C. After the steerable distal portion 504 has passed, the wall of the colon C maintains the curve in the flexible body 502 of the colonoscope 500 as it is advanced. Friction develops along the body 502 of the colonoscope 500 as it is inserted, particularly at each turn in the colon C. Because of the friction, when the user attempts to advance the colonoscope 500, the body 502' tends to move outward at each curve, pushing against the wall of the colon C, which exacerbates the problem by increasing the friction and making it more difficult to advance the colonoscope 500. On the other hand, when the colonoscope 500 is withdrawn, the body 502" tends to move inward at each curve taking up the slack that developed when the colonoscope 500 was advanced. When the patient's colon C is extremely tortuous, the distal end of the body 502 becomes unresponsive to the user's manipulations, and eventually it may become impossible to advance the colonoscope 500 any farther. In addition to the difficulty that it presents to the user, tortuosity of the patient's colon also increases the risk of complications, such as intestinal perforation.

Figure 2:
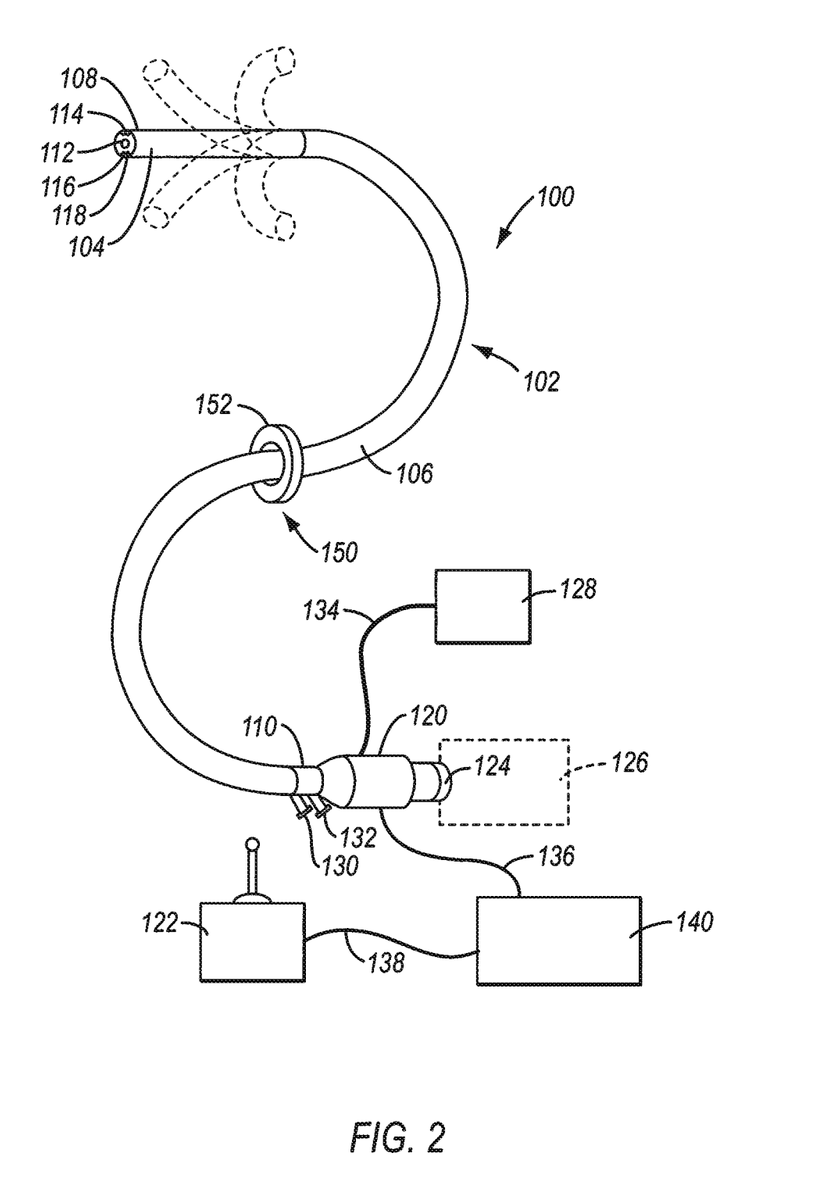
FIG. 2 shows a first embodiment of the steerable endoscope of the present invention.

FIG. 2 shows a first embodiment of the steerable endoscope 100 of the present invention. The endoscope 100 has an elongate body 102 with a manually or selectively steerable distal portion 104 and an automatically controlled proximal portion 106. The selectively steerable distal portion 104 can be selectively steered or bent up to a full 180 degree bend in any direction. A fiberoptic imaging bundle 112 and one or more illumination fibers 114 extend through the body 102 from the proximal end 110 to the distal end 108. Alternatively, the endoscope 100 can be configured as a video endoscope with a miniaturized video camera, such as a CCD camera, positioned at the distal end 108 of the endoscope body 102. The images from the video camera can be transmitted to a video monitor by a transmission cable or by wireless transmission. Optionally, the body 102 of the endoscope 100 may include one or two instrument channels 116, 118 that may also be used for insufflation or irrigation. The body 102 of the endoscope 100 is highly flexible so that it is able to bend around small diameter curves without buckling or kinking. When configured for use as a colonoscope, the body 102 of the endoscope 100 is typically from 135 to 185 cm in length and approximately 1243 mm in diameter. The endoscope 100 can be made in a variety of other sizes and configurations for other medical and industrial applications.

A proximal handle 120 is attached to the proximal end 110 of the elongate body 102. The handle 120 includes an ocular 124 connected to the fiberoptic imaging bundle 112 for direct viewing and/or for connection to a video camera 126. The handle 120 is connected to an illumination source 128 by an illumination cable 134 that is connected to or continuous with the illumination fibers 114. A first luer lock fitting, 130 and a second luer lock fitting 132 on the handle 120 are connected to the instrument channels 116, 118.

The handle 120 is connected to an electronic motion controller 140 by way of a controller cable 136. A steering control 122 is connected to the electronic motion controller 140 by way of a second cable 13 M. The steering control 122 allows the user to selectively steer or bend the selectively steerable distal portion 104 of the body 102 in the desired direction. The steering control 122 may be a joystick controller as shown, or other known steering control mechanism. The electronic motion controller 140 controls the motion of the automatically controlled proximal portion 106 of the body 102. The electronic motion controller 140 may be implemented using a motion control program running on a microcomputer or using an application-specific motion controller. Alternatively, the electronic motion controller 140 may be implemented using, a neural network controller.

An axial motion transducer 150 is provided to measure the axial motion of the endoscope body 102 as it is advanced and withdrawn. The axial motion transducer 150 can be made in many possible configurations. By way of example, the axial motion transducer 150 in FIG. 2 is configured as a ring 152 that surrounds the body 102 of the endoscope 100. The axial motion transducer 150 is attached to a fixed point of reference, such as the surgical table or the insertion point for the endoscope 100 on the patient's body. As the body 102 of the endoscope 100 slides through the axial motion transducer 150, it produces a signal indicative of the axial position of the endoscope body 102 with respect to the fixed point of reference and sends a signal to the electronic motion controller 140 by telemetry or by a cable (not shown). The axial motion transducer 150 may use optical, electronic or mechanical means to measure the axial position of the endoscope body 102. Other possible configurations for the axial motion transducer 150 are described below.

Figure 3:
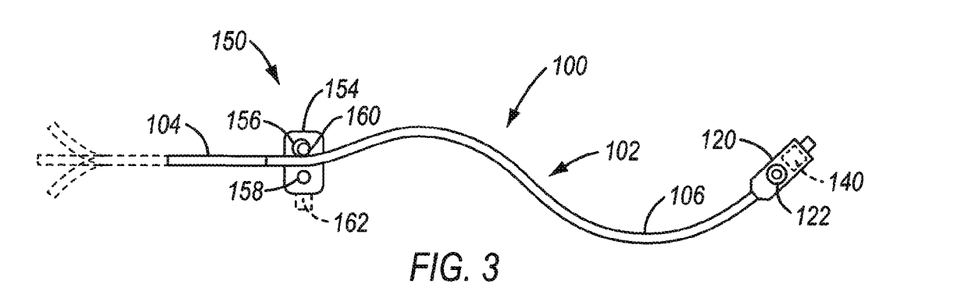
FIG. 3 shows a second embodiment of the steerable endoscope of the present invention.

FIG. 3 shows a second embodiment of the endoscope 100 of the present invention. As in the embodiment of FIG. 2, the endoscope 100 has an elongate body 102 with a selectively steerable distal portion 104 and an automatically controlled proximal portion 106. The steering control 122 is integrated into proximal handle 120 in the form or one or two dials for selectively steering, the selectively steerable distal portion 104 of the endoscope 100. Optionally, the electronic motion controller 140 may be miniaturized and integrated into proximal handle 120, as well. In this embodiment, the axial motion transducer 150 is configured with a base 154 that is attachable to a fixed point of reference, such as the surgical table. A first roller 156 and a second roller 158 contact the exterior of the endoscope body 102. A multi-turn potentiometer 160 or other motion transducer is connected to the first roller 156 to measure the axial motion of the endoscope body 102 and to produce a signal indicative of the axial position.

The endoscope 100 may be manually advanced or withdrawn by the user by grasping the body 102 distal to the axial motion transducer 150. Alternatively, the first roller 156 and/or second roller 158 may be connected to a motor 162 for automatically advancing and withdrawing the body 102 of the endoscope 100.

Figure 4:
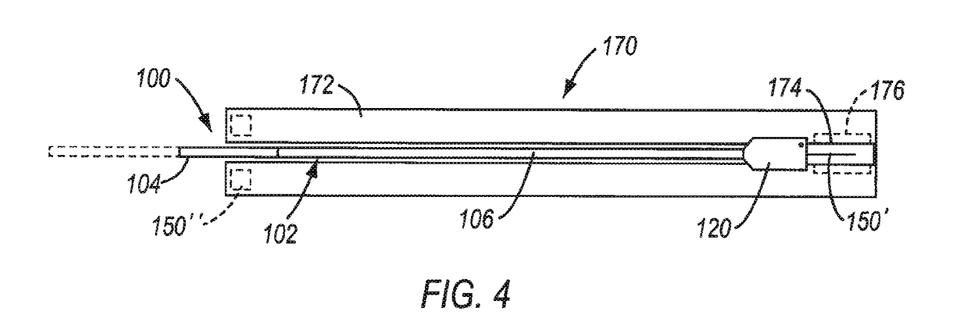
FIG. 4 shows a third embodiment of the steerable endoscope of the present invention.

FIG. 4 shows a third embodiment of the endoscope 100 of the present invention, which utilizes an elongated housing 170 to organize and contain the endoscope 100. The housing 170 has a base 172 with a linear track 174 to guide the body 102 of the endoscope 100. The housing 170 may have an axial motion transducer 150' that is configured as a linear motion transducer integrated into the linear track 174. Alternatively, the housing, 170 may have an axial motion transducer 150'' configured similarly to the axial motion transducer 150 in FIG. 2 or 3. The endoscope 100 may be manually advanced or withdrawn by the user by grasping the body 102 distal to the housing 170. Alternatively, the housing 170 may include a motor 176 or other linear motion actuator for automatically advancing and withdrawing the body 102 of the endoscope 100. In another alternative configuration, a motor with friction wheels, similar to that described above in connection with FIG. 3, may be integrated into the axial motion transducer 150''.

Figure 5:
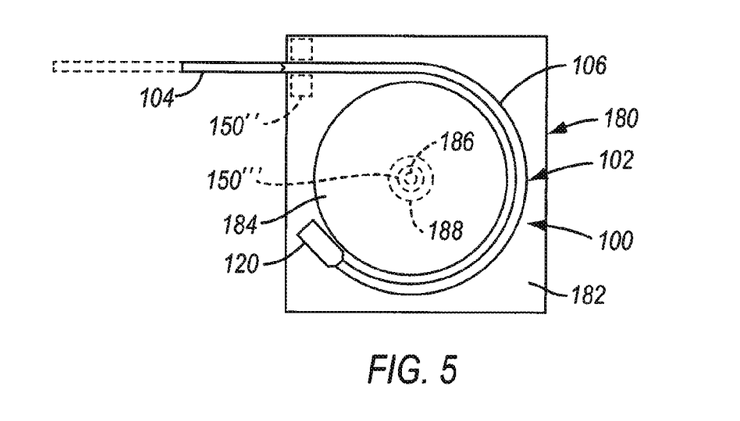
FIG. 5 shows a fourth embodiment of the steerable endoscope of the present invention.

FIG. 5 shows a fourth embodiment of the endoscope 100 of the present invention, which utilizes a rotary housing 180 to organize and contain the endoscope 100. The housing 180 has a base 182 with a rotating drum 184 to guide the body 102 of the endoscope 100. The housing 180 may have an axial motion transducer 150'' that is configured as a potentiometer connected to the pivot axis 186 of the rotating drum 184. Alternatively, the housing 180 may have an axial motion transducer 150'' configured similarly to the axial motion transducer 150 in FIG. 2 or 3. The endoscope 100 may be manually advanced or withdrawn by the user by grasping the body 102 distal to the housing 180. Alternatively, the housing 180 may include a motor 188 connected to the rotating drum 184 for automatically advancing and withdrawing the body 102 of the endoscope 100. In another alternative configuration, a motor with friction wheels, similar to that described above in connection with FIG. 3, may be integrated into the axial motion transducer 150''.

Figure 6:
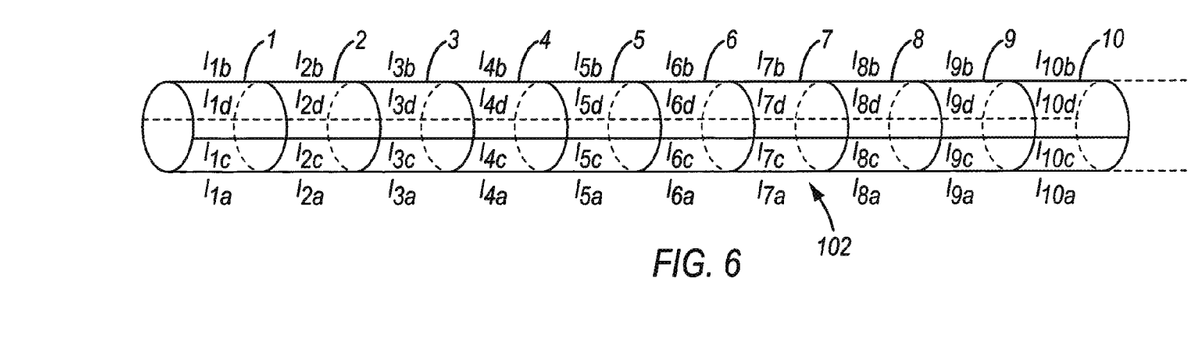
FIG. 6 shows a wire frame model of a section of the body of the endoscope in a neutral or straight position.

FIG. 6 shows a wire frame model of a section of the body 102 of the endoscope 100 in a neutral or straight position. Most of the internal structure of the endoscope body 102 has been eliminated in this drawing for the sake of clarity. The endoscope body 102 is divided up into sections 1, 2, 3 . . . 10, etc. The geometry of each section is defined by four length measurements along the a, b, c and d axes. For example, the geometry of section 1 is defined by the four length measurements $l_{1a}, l_{1b}, l_{1c}, l_{1d}$, and the geometry of section 2 is defined by the four length measurements $l_{2a}, l_{2b}, l_{2c}, l_{2d}$, etc. Preferably, each of the length measurements is individually controlled by a linear actuator (not shown). The linear actuators may utilize one of several different operating principles. For example, each of the linear actuators may be a self-heating NiTi alloy linear actuator or an electrorheological plastic actuator, or other known mechanical, pneumatic, hydraulic or electromechanical actuator. The geometry of each section may be altered using the linear actuators to change the four length measurements along the a, b, c and d axes. Preferably, the length measurements are changed in complementary pairs to selectively bend the endoscope body 102 in a desired direction. For example, to bend the endoscope body 102 in the direction of a axis, the measurements $l_{1a}, l_{2a}, l_{3a} \ldots l_{10a}$ would be shortened and the measurements $l_{1b}, l_{2b}, l_{3b} \ldots l_{10b}$ would be lengthened an equal amount. The amount by which these measurements are changed determines the radius of the resultant curve.

In the selectively steerable distal portion 104 of the endoscope body 102, the linear actuators that control the a, b, c and d axis measurements of each section are selectively controlled by the user through the steering control 122. Thus, by appropriate control of the a, b, c and d axis measurements, the selectively steerable distal portion 104 of the endoscope body 102 can be selectively steered or bent up to a full 180 degrees in any direction.

Figure 7:
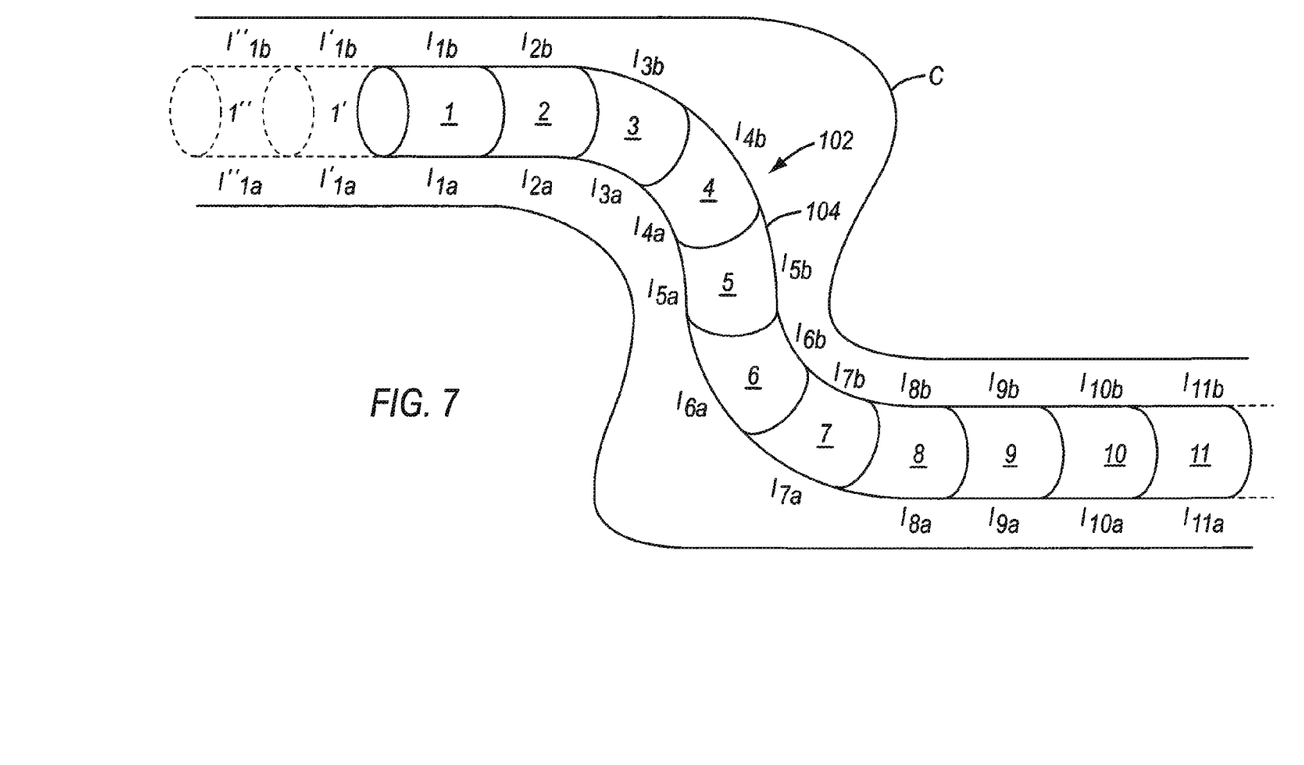
FIG. 7 shows the wire frame model of the endoscope body shown in FIG. 6 passing through a curve in a patient's colon.

In the automatically controlled proximal portion 106, however, the a, b, c and d axis measurements of each section are automatically controlled by the electronic motion controller 140, which uses a curve propagation method to control the shape of the endoscope body 102. To explain how the curve propagation method operates, FIG. 7 shows the wire frame model of a part of the automatically controlled proximal portion 106 of the endoscope body 102 shown in FIG. 6 passing, through a curve in a patient's colon C. For simplicity, an example of a two-dimensional curve is shown and only the a and b axes will be considered. In a three-dimensional curve all four of the a, b, c and d axes would be brought into play.

In FIG. 7, the endoscope body 102 has been maneuvered through the curve in the colon C with the benefit of the selectively steerable distal portion 104 (this part of the procedure is explained in more detail below) and now the automatically controlled proximal portion 106 resides in the curve. Sections 1 and 2 are in a relatively straight part of the colon C, therefore $l_{1a}=l_{1b}$ and $l_{2a}=l_{2b}$. However, because sections 3-7 are in the S-shaped curved section, $l_{3a}<l_{3b}$, $l_{4a}<l_{4b}$ and $l_{5a}<l_{5b}$, but $l_{6a}>l_{6b}$, $l_{7a}>l_{7b}$ and $l_{8a}>l_{8b}$. When the endoscope body 102 is advanced distally by one unit, section 1 moves into the position marked 1', section 2 moves into the position previously occupied by section 1, section 3 moves into the position previously occupied by section 2, etc. The axial motion transducer 150 produces a signal indicative of the axial position of the endoscope body 102 with respect to a fixed point of reference and sends the signal to the electronic motion controller 140, Under control of the electronic motion controller 140, each time the endoscope body 102 advances one unit, each section in the automatically controlled proximal portion 106 is signaled to assume the shape of the section that previously occupied the space that it is now in. Therefore, when the endoscope body 102 is advanced to the position marked 1", $l_{1a}=l_{1b}$, $l_{2a}=l_{2b}$, $l_{3a}=l_{3b}$, $l_{4a}<l_{4b}$, $l_{5a}<l_{5b}$, $l_{6a}<l_{6b}$, $l_{7a}>l_{7b}$, and $l_{8a}>l_{8b}$, and $l_{9a}>l_{9b}$ when the endoscope body 102 is advanced to the position marked 1''', $l_{1a}=l_{1b}$, $l_{2a}=l_{2}$, $l_{3a}=l_{3b}$, $l_{4a}=l_{4b}$, $l_{5a}<l_{5b}$, $l_{6a}<l_{6b}$, $l_{7a}<l_{7b}$, $l_{8a}>l_{8b}$, $l_{9a}>l_{9b}$, and $l_{10a}>l_{10b}$. Thus, the S-shaped curve propagates proximally along the length of the automatically controlled proximal portion 106 of the endoscope body 102. The S-shaped curve appears to be fixed in space, as the endoscope body 102 advances distally.

Similarly, when the endoscope body 102 is withdrawn proximally, each time the endoscope body 102 is moved proximally by one unit, each section in the automatically controlled proximal portion 106 is signaled to assume the shape of the section that previously occupied the space that it is now in. The S-shaped curve propagates distally along the length of the automatically controlled proximal portion 106 of the endoscope body 102, and the S-shaped curve appears to be fixed in space, as the endoscope body 102 withdraws proximally.

Whenever the endoscope body 102 is advanced or withdrawn, the axial motion transducer 150 detects the change in position and the electronic motion controller 140 propagates the selected curves proximally or distally along the automatically controlled proximal portion 106 of the endoscope body 102 to maintain the curves in a spatially fixed position. This allows the endoscope body 102 to move through tortuous curves without putting unnecessary force on the wall of the colon C.

Figure 8:
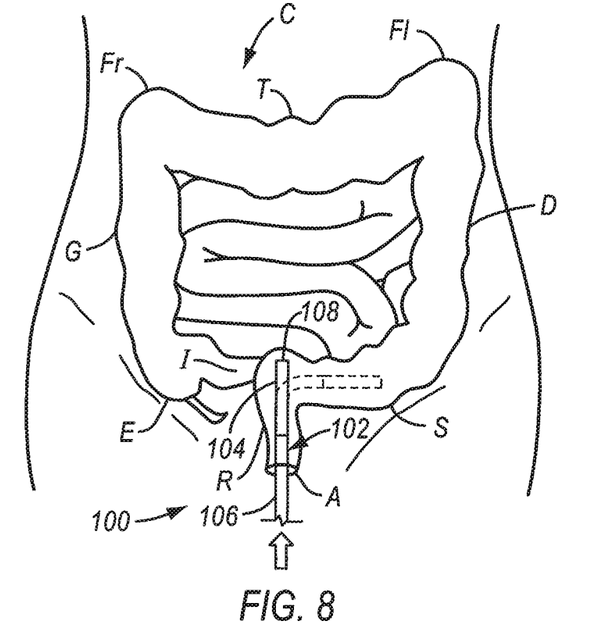
FIGS. 8-13 show the endoscope of the present invention being employed for a colonoscopic examination of a patient's colon.

FIGS. 8-13 show the endoscope 100 of the present invention being employed for a colonoscopic examination of a patient's colon. In FIG. 8, the endoscope body 102 has been lubricated and inserted into the patient's colon C through the anus A. The distal end 108 of the endoscope body 102 is advanced through the rectum R until the first turn in the colon C is reached, as observed through the ocular 124 or on a video monitor. To negotiate the turn, the selectively steerable distal portion 104 of the endoscope body 102 is manually steered toward the sigmoid colon S by the user through the steering control 122. The control signals from the steering control 122 to the selectively steerable distal portion 104 are monitored b the electronic y motion controller 140. When the correct curve of the selectively steerable distal portion 104 for advancing the distal end 108 of the endoscope body 102 into the sigmoid colon S has been selected, the curve is logged into the memory of the electronic motion controller 140 as a reference. This step can be performed in a manual mode, in which the user gives a command to the electronic motion controller 140 to record the selected curve, using keyboard commands or voice commands. Alternatively, this step can be performed in an. automatic mode, in which the user signals to the electronic, motion controller 140 that the desired curve has been selected by advancing the endoscope body 102 distally.

Whether operated in manual mode or automatic mode, once the desired curve has been selected with the selectively steerable distal portion 104, the endoscope body 102 is advanced distally and the selected curve is propagated proximally along the automatically controlled proximal portion 106 of the endoscope, body 102 by the electronic motion controller 140, as described above. The curve remains fixed in space while the endoscope body 102 is advanced distally through the sigmoid colon S. In a particularly tortuous colon, the selectively steerable distal portion 104 may have to be steered through multiple curves to traverse the sigmoid colon S.

Figure 9:
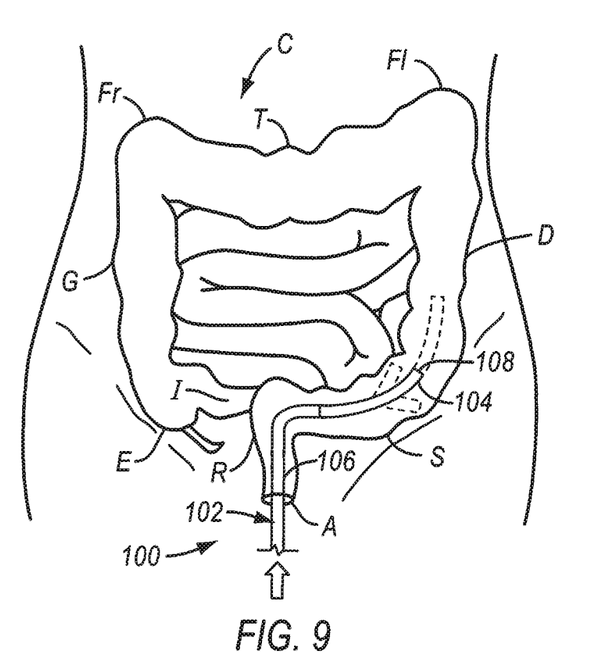
Figure 10:
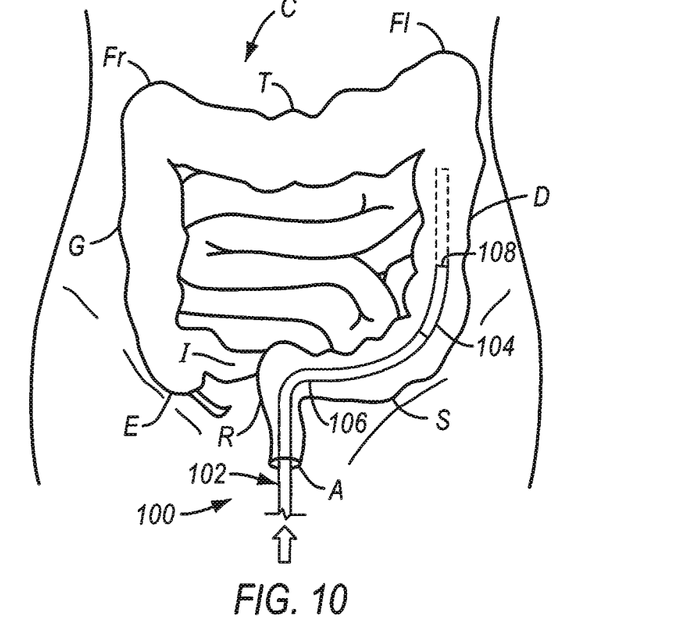

As illustrated in FIG. 9, the user may stop the endoscope 100 at any point for examination or treatment of the mucosal surface or any other features within the colon C. The selectively steerable distal portion 104 may be steered in any direction to examine the inside of the colon C. When the user has completed the examination of the sigmoid colon S, the selectively steerable distal portion 104 is steered in a superior direction toward the descending colon D. Once the desired curve has been selected with the selectively steerable distal portion 104, the endoscope body 102 is advanced distally into the descending colon D, and the second curve as well as the first curve are propagated proximally along the automatically controlled proximal portion 106 of the endoscope body 102, as shown in FIG. 10.

If, at any time, the user decides that the path taken by the endoscope body 102 needs to be revised or corrected, the endoscope 100 may be withdrawn proximally and the electronic motion controller 140 commanded to erase the previously selected curve. This can be done manually using keyboard commands or voice commands or automatically by programming the electronic motion controller 140 to go into a revise mode when the endoscope body 102 is withdrawn a certain distance. The revised or corrected curve is selected using the selectively steerable distal portion 104, and the endoscope body 102 is advanced as described before.

Figure 11:
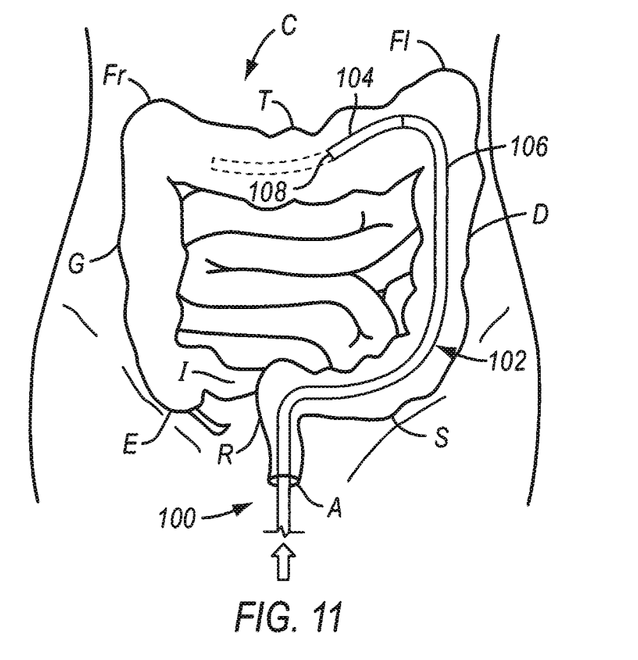
Figure 12:
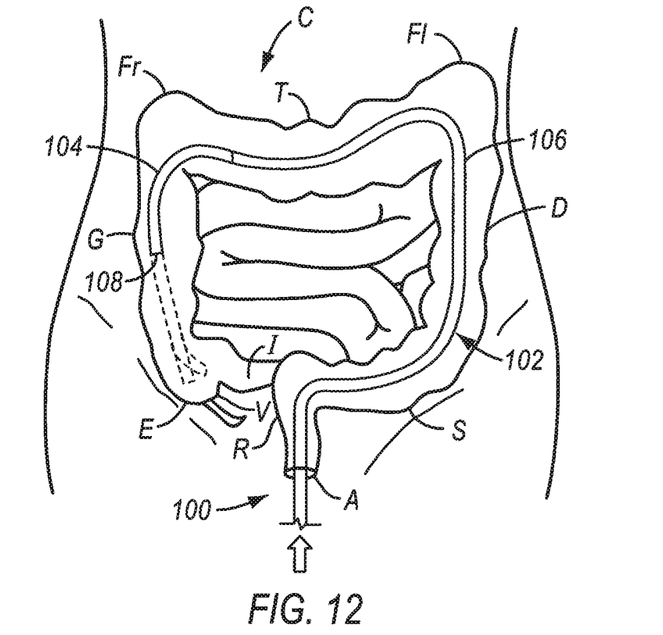

The endoscope body 102 is advanced through the descending colon D until it reaches the left (splenic) flexure $F_l$ of the colon. Here, in many cases, the endoscope body 102 must negotiate an almost 180 degree hairpin turn. As before, the desired curve is selected using the selectively steerable distal portion 104, arid the. endoscope body 102 is advanced distally through the transverse colon T, as shown in FIG. 11. Each of the previously selected curves is propagated proximally along the automatically controlled proximal portion 106 of the endoscope body 102. The same procedure is followed at the right (hepatic) flexure $F_r$ of the colon and the distal end 108 of the endoscope body 102 is advanced through the ascending colon G to the cecum E, as shown in FIG. 12. The cecum E, the ileocecal valve V and the terminal portion of the ileum I can be examined from this point using, the selectively steerable distal portion 104 of the endoscope body 102.

Figure 13:
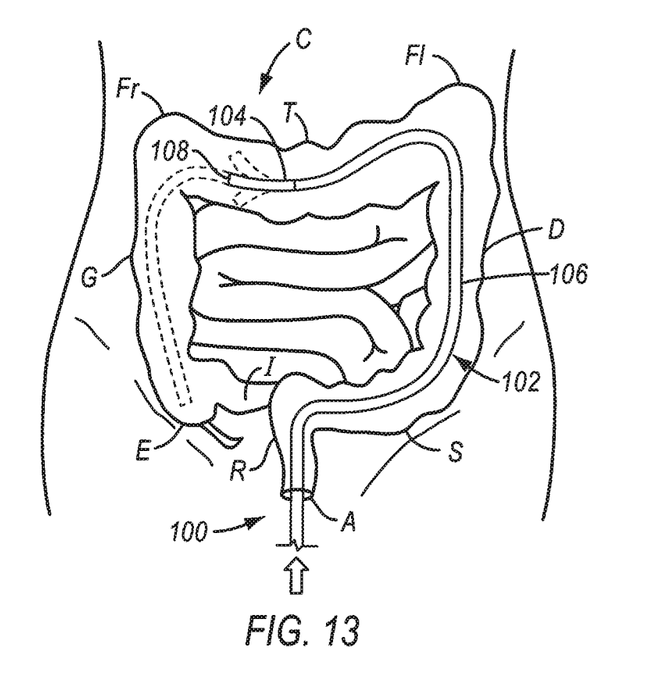

FIG. 13 shows the endoscope 100 being, withdrawn through the colon C. As the endoscope 100 is withdrawn, the endoscope body 102 follows the previously selected curves by propagating the curves distally along the automatically controlled proximal portion 106, as described above. At any point, the user may stop the endoscope 100 for examination or treatment of the mucosal surface or any other features within the colon C using the selectively steerable distal portion 104 of the endoscope body 102.

In one preferred method according to the present invention, the electronic motion controller 140 includes an electronic memory in which is created a three-dimensional mathematical model of the patient's colon or other anatomy through which the endoscope body 102 is maneuvered. The three-dimensional model can be annotated by the operator to record the location of anatomical landmarks, lesions, polyps, biopsy samples and other features of interest. The three-dimensional model of the patient's anatomy can be used to facilitate reinsertion of the endoscope body 102 in subsequent procedures. In addition, the annotations can be used to quickly find the location of the features of interest. For example, the three-dimensional model can be annotated with the location where a biopsy sample was taken during an exploratory endoscopy. The site of the biopsy sample can be reliably located again in follow-up procedures to track the progress of a potential disease process and/or to perform a therapeutic procedure at the site.

In one particularly preferred variation of this method, the electronic motion controller 140 can be programmed, based on the three-dimensional model in the electronic memory, so that the endoscope body 102 will automatically assume the proper shape to follow the desired path as it is advanced through the patient's anatomy. In embodiments of the steerable endoscope 100 that are configured for automatically advancing and withdrawing the endoscope body 102, as described above in connection with FIGS. 3, 4 and 5, the endoscope body 102 can be commanded to advance automatically though the patient's anatomy to the site of a previously noted lesion or other point of interest based on the three-dimensional model in the electronic memory.

Imaging software would allow the three-dimensional model of the patient's anatomy obtained using the steerable endoscope 100 to be viewed on a computer monitor or the like. This would facilitate comparisons between the three-dimensional model and images obtained with other imaging modalities, for example fluoroscopy, radiography, ultrasonography, magnetic resonance imaging (MRI), computed tomography (CT scan), electron beam tomography or virtual colonoscopy. Conversely, images from these other imaging modalities can be used to map out an approximate path or trajectory to facilitate insertion of the endoscope body 102. In addition, images from other imaging modalities can be used to facilitate locating suspected lesions with the steerable endoscope 100. For example, images obtained using a barium-contrast radiograph of the colon can be used to map out an approximate path to facilitate insertion of the endoscope body 102 into the patient's colon. The location and depth of any suspected lesions seen on the radiograph can be noted so that the endoscope body 102 can be quickly and reliably guided to the vicinity of the lesion.

Imaging modalities that provide three-dimensional information, such as biplanar fluoroscopy, CT or MRI, can be used to program the electronic motion controller 140 so that the endoscope body 102 will automatically assume the proper shape to follow the desired path as it is advanced through the patient's anatomy. In embodiments of the steerable endoscope 100 that are configured for automatically advancing and withdrawing the endoscope body 102, the endoscope body 102 can be commanded to advance automatically though the patient's anatomy along the desired path as determined by the three-dimensional imacrinc, information. Similarly, the endoscope body 102 can be commanded to advance automatically to the site of a suspected lesion or other point of interest noted on the images.

Although the endoscope of the present invention has been described for use as a colonoscope, the endoscope can be configured for a number of other medical and industrial applications. In addition, the present invention can also be configured as a catheter, cannula, surgical instrument or introducer sheath that uses the principles of the invention for navigating through tortuous body channels.

In a variation of the method that is particularly applicable to laparoscopy or thoracoscopy procedures, the steerable endoscope 100 can be selectively maneuvered along a desired path around and between organs in a patient's body cavity. The distal end 108 of the endoscope 100 is inserted into the patient's body cavity through a natural opening, through a surgical incision or through a surgical cannula or introducer. The selectively steerable distal portion 104 can be used to explore and examine the patient's body cavity and to select a path around and between the patient's organs. The electronic motion controller 140 can be used to control the automatic ally controlled proximal portion 106 of the endoscope body 102 to follow the selected path and, if necessary, to return to a desired location using the three-dimensional model in the electronic memory of the electronic motion controller 140.

While the present invention has been described herein with respect to the exemplary embodiments and the best mode for practicing the invention, it will be apparent to one of ordinary skill in the art that man modifications, improvements and subcombinations of the various embodiments, adaptations and variations can be made to the invention without departing from the spirit and scope thereof.

I claim:

1. A method of controlling a steerable instrument, comprising:
    storing in electronic memory a three-dimensional model of a path traversed by the instrument in a patient's anatomy, wherein the three-dimensional model is based upon signals obtained from maneuvering a length of the instrument distally along the path in the patient's anatomy;
    annotating the three-dimensional model to indicate a location of a feature of interest along the path;
    withdrawing the instrument proximally along the path in the patient's anatomy; and
    after the withdrawing, automatically controlling the instrument to advance distally along the path in the patient's anatomy to return to the location of the feature of interest according to the annotated three-dimensional model.

2. The method of claim 1, wherein the withdrawing step includes withdrawing the instrument completely from a patient's body.

3. The method of claim 2, further comprising reinserting the instrument into the patient's anatomy prior to controlling the instrument to return to the location of the feature of interest.

4. The method of claim 1, wherein the withdrawing step includes partially withdrawing the instrument from a patient's body.

5. The method of claim 1, wherein the feature of interest is chosen from at least one of an anatomical landmark, a lesion, a polyp, and a location from which a biopsy sample was taken.

6. The method of claim 1, wherein the automatically controlling the instrument to advance distally along the path in the patient's anatomy to return to the location of the feature of interest is performed via an electronic motional controller programmed to control a shape of the instrument to follow the three-dimensional model.

7. The method of claim 1, further comprising, prior to storing the three dimensional model, selectively steering a distal portion of the instrument to assume a selected curve, advancing the instrument distally along the path in the patient's anatomy, and controlling a proximal portion of the instrument to assume the selected curve of the distal portion after the advancing.

8. The method of claim 7, wherein advancing the instrument distally along the path in the patient's anatomy includes measuring an axial position of the instrument.

9. The method of claim 8, wherein measuring the axial position of the instrument comprises measuring the axial position via an axial motion transducer.

10. The method of claim 7, further comprising providing an axial position signal via the axial motion transducer to an electronic motion controller that automatically controls the instrument during the controlling step.

11. The method of claim 7, wherein controlling the proximal portion of the instrument comprises controlling the proximal portion such that the selected curve remains approximately fixed in space as the instrument is advanced distally or withdrawn proximally.

12. The method of claim 7, wherein the selected curve is fixed relative to a fixed point of reference while advancing the instrument distally or withdrawing the instrument proximally.

13. The method of claim 7, wherein the proximal portion includes a plurality of segments, wherein adjacent segments of the plurality of segments are pivotally coupled to each other.

14. The method of claim 1, wherein the patient's anatomy includes at least a part of the patient's colon.

15. The method of claim 1, wherein the instrument is a colonoscope.

16. The method of claim 1, wherein a motor withdraws the instrument and advances the instrument.

* * * * *